(12) United States Patent
Kamimura et al.

(10) Patent No.: US 11,008,566 B2
(45) Date of Patent: May 18, 2021

(54) METHOD FOR OBTAINING ANTIBODY (71) Applicant: Chiome Bioscience Inc., Tokyo (JP)

(72) Inventors: Yosuke Kamimura, Tokyo (JP); Kotaro Yamamoto, Tokyo (JP)

(73) Assignee: Chiome Bioscience Inc., Tokyo (JP)

( * ) Notice: Subject to any disclaimer, the term of this patent is extended or adjusted under 35 U.S.C. 154(b) by 303 days.

(21) Appl. No.: 16/334,702

(22) PCT Filed: Sep. 29, 2017

(86) PCT No.: PCT/JP2017/035504
§ 371 (c)(1),
(2) Date: Mar. 19, 2019

(87) PCT Pub. No.: WO2018/062495
PCT Pub. Date: Apr. 5, 2018

(65) Prior Publication Data
US 2019/0233811 A1 Aug. 1, 2019

(30) Foreign Application Priority Data

Sep. 30, 2016 (JP) .............................. JP2016-192472

(51) Int. Cl.
| | |
|---|---|
| *C07K 16/46* | (2006.01) |
| *G01N 33/68* | (2006.01) |
| *C12N 15/10* | (2006.01) |
| *C40B 30/06* | (2006.01) |
| *C40B 30/04* | (2006.01) |
| *C12P 21/00* | (2006.01) |
| *C07K 16/00* | (2006.01) |
| *C12N 15/09* | (2006.01) |

(52) U.S. Cl.
CPC .......... *C12N 15/1037* (2013.01); *C07K 16/00* (2013.01); *C07K 16/46* (2013.01); *C12P 21/005* (2013.01); *C40B 30/04* (2013.01); *C40B 30/06* (2013.01); *G01N 33/6854* (2013.01); *C12N 15/09* (2013.01)

(58) Field of Classification Search
None
See application file for complete search history.

(56) References Cited

U.S. PATENT DOCUMENTS

| | | | | |
|---|---|---|---|---|
| 6,465,251 | B1 * | 10/2002 | Schultze | C12N 5/0635 435/2 |
| 2006/0183225 | A1 | 8/2006 | Ohta et al. | |
| 2011/0070650 | A1 | 3/2011 | Ohta et al. | |
| 2014/0287402 | A1 | 9/2014 | Garrone et al. | |
| 2017/0058029 | A1 | 3/2017 | Hashimoto et al. | |

FOREIGN PATENT DOCUMENTS

| | | |
|---|---|---|
| EP | 1559318 A1 | 8/2005 |
| EP | 3581645 A1 | 12/2019 |
| JP | 4214234 B | 1/2009 |
| JP | 2009-060850 A | 3/2009 |
| JP | 4478577 B | 6/2010 |
| JP | 4487068 B | 6/2010 |
| JP | 2014-518080 A | 7/2014 |
| WO | WO 2004/011644 A1 | 2/2004 |
| WO | WO 2008/047480 A1 | 4/2008 |
| WO | WO 2015/167011 A1 | 11/2015 |

OTHER PUBLICATIONS

Kanehiro et al., "In vitro antibody screening system using a chicken B cell line, DT40-SW: Improvement of mutation frequency" The Society for Bioscience and Bioengineering, Japan, 3Cal12.
Kaymakcalan et al, "Comparisons of affinities, avidities, and complement activation of adalimumab, infliximab, and etanercept in binding to soluble and membrane tumor necrosis factor", Clinical Immunology (2009) 131, 308-316.
Papadopoulos et al., "Binding and neutralization of vascular endothelial growth factor (VEGF) and related ligands by VEGF Trap, ranibizumab and bevacizumab" Angiogenesis (2012) 15:171-185.
Seo et al., "Rapid generation of specific antibodies by enhanced homologous recombination", Nature Biotechnology, vol. 23, No. 6, Jun. 2005.
Sigal et al., "Cyclosporin A, FK-506, and Rapamycin: Pharmacologic Probes of Lymphocyte Signal Transduction", Annu. Rev.Immunol. 1992. 10:519-60.
Manez, et al., Comparative Evaluation of 1-8 Tacrolimus (FK506) and Cyclosporin a as Immunosuppressive Agents, Transplantation Reviews, Apr. 1995, vol. 9, No. 2, pp. 63-76.
Sigal, et al., Cyclosporin A, FK-506, and Rapamycin: Pharmacologic Probes of Lymphocyte Signal Transduction, Annu. Rev. Immunol., 1992, vol. 10, pp. 519-560.
International Search Report issued in application No. PCT/JP2017/035504, dated Jan. 9, 2018.
Extended European Search Report in European Patent Application No. 17856444.9 dated Apr. 28, 2020.
Heidt et al. Caldneurin inhibitors affect B cell antibody responses indirectly by interfering with T cell help. Journal of Translational Immunology, vol. 159, pp. 199-207, Oct. 13, 2009.
Wicker et al. Suppression of B cell activation by cyclosporin A, FK506 and rapamycin. Article, European Journal of Immunology, vol. 20, pp. 2277-2283, 1990.

* cited by examiner

*Primary Examiner* — Daniel C Gamett
(74) *Attorney, Agent, or Firm* — Knobbe, Martens, Olson & Bear LLP (57) ABSTRACT

The present invention relates to a method for obtaining an antibody from an avian B cell antibody library, comprising the following steps (a) to (d):
(a) a step of allowing an avian B cell antibody library to come into contact with an antigen in the presence of a calcineurin inhibitor and avian serum,
(b) a step of selecting avian B cells that bind to the antigen in the step (a),
(c) a step of culturing the avian B cells selected in the step (b) in the presence of a calcineurin inhibitor and avian serum, and
(d) a step of obtaining the avian B cells obtained through the step (c) and/or an antibody expressed by the avian B cells.

8 Claims, 5 Drawing Sheets

Common

METHOD FOR OBTAINING ANTIBODY

CROSS REFERENCE TO RELATED APPLICATIONS

This application is a U.S. National Phase Application of PCT International Application Number PCT/JP2017/035504, filed on Sep. 29, 2017, designating the United States of America and published in the Japanese language, which is an International Application of and claims the benefit of priority to Japanese Patent Application No. 2016-192472, filed on Sep. 30, 2016. The disclosures of the above-referenced applications are hereby expressly incorporated by reference in their entireties.

TECHNICAL FIELD

The present invention relates to a method for obtaining an antibody. More specifically, the present invention relates to a method for obtaining an antibody binding to an antigen with high affinity from an antibody library.

BACKGROUND ART

Antibody as a main component binds to a specific antigen in a living body and provokes various biological defense reactions. Antibody drug is a therapeutic agent that utilizes the aforementioned properties of an antibody, and thus, a therapeutic antibody is required to have high antigen specificity and high affinity to a target antigen.

The affinity of an antibody to an antigen is often indicated as a dissociation constant KD. The commonly used analysis method is Surface Plasmon Resonance (SPR). According to kinetic analysis, an association rate constant (ka value or kon value) and a dissociation rate constant (kd value or koff value) are measured, and KD is then calculated. A monoclonal antibody as a candidate for the development of pharmaceutical products is required to have a KD value of $1 \times 10^{-8}$ M or less. For example, Humira (registered trademark) and Lucentis (registered trademark), which have been used as antibody drugs, are high-affinity antibodies having KD of $3.0 \times 10^{-11}$ M and $4.6 \times 10^{-11}$ M, respectively (Non Patent Literatures 1 and 2).

Antibody production methods are classified into methods of utilizing animal immunization and methods of not utilizing animal immunization. As a method of utilizing animal immunization, a hybridoma method comprising immunizing an animal with an antigen and then fusing the obtained B cells with myelomas has been applied, for example. However, this method has been problematic in that time and effort are required to obtain an antibody because animals are utilized, and in that an antibody cannot be obtained due to immune tolerance in some cases. As a method of not utilizing animal immunization, a phage display method has been applied, for example. This is a method comprising presenting a single chain antibody consisting of an antibody variable region (single chain variable fragment; scFv) to phage particles to obtain a clone binding to a target antigen. However, this method has been problematic in that the quality of a library depends on a diversity of scFv, and in that changes in specificity or affinity are generated in the process of converting scFv to a full-length antibody.

In addition to the above-described techniques of producing antibodies, a technique of producing antibodies by utilizing a chicken B cell-derived DT40 cell line, ADLib (registered trademark) System, has been developed, and it has become possible to utilize a library capable of generating human antibodies according to gene transfer (Patent Literatures 1, 2 and 3, and Non Patent Literature 3). Since a clone having an antibody specifically binding to an antigen can be selected from a library according to this system, immune tolerance can be avoided, and a full-length antibody can be promptly obtained. What is more, since a diversification of antibody gene sequences mainly occurs as a result of homologous recombination (gene conversion) in birds, this system is advantageous in that changes in antibody gene sequences can be expected according to a mechanism different from diversification of human or mice.

Several means for obtaining high-affinity antibodies have already been carried out, but at the same time, such means have various problems. In animal immunization, a method of repeatedly immunizing an animal with the same antigen to induce B cells expressing high-affinity antibodies, which is called "multiple immunizations," has been applied. However, this method requires time and effort, and also, is likely to increase non-specific binding. In the phage display method, a method of repeatedly selecting an antibody clone binding to a target antigen to concentrate a clone with high affinity has been applied. However, there may be some cases where a single chain antibody with high affinity loses its affinity, when it is changed to a full-length antibody. Moreover, a method of randomly introducing a mutation into the sequence of an antibody variable region obtained by each method, so to as obtain a high-affinity antibody, has also been used. However, affinity is not necessarily improved. Otherwise, while affinity is improved, non-specific bonds are likely to increase, or it is likely that the obtained antibody cannot be properly expressed and/or functioned as a result of the introduced mutation.

Other than the aforementioned methods, a method of promoting the diversification of sequences to obtain a high-affinity antibody has also been developed. Examples of such a method include: methods of utilizing: animal immunization of using GANP mice (registered trademark), in which many somatic mutations are induced in the antibody variable region of germinal center B cells, in comparison to normal wild-type mice (Patent Literature 4); avian B cells comprising an inactivated XRCC3 gene (Patent Literature 5); avian B cells in which the expression of an AID gene has been controlled (Patent Literature 6); or a DT40-SWΔC cell line, into which mutant AID with enhanced AID activity associated with mutation introduction has been introduced (Non Patent Literature 4). However, all of these methods are not always directly linked to the improvement of affinity.

As mentioned above, regarding antibody drugs, it is an extremely important object to obtain an antibody having high affinity, and therefore, it has been desired to develop a method for simply obtaining such an antibody having high affinity with high probability.

CITATION LIST

Patent Literature

Patent Literature 1: Japanese Patent No. 4214234
Patent Literature 2: WO2008/047480
Patent Literature 3: WO2015/167011
Patent Literature 4: Japanese Patent No. 4478577
Patent Literature 5: JP Patent Publication (Kokai) No. 2009-060850 A
Patent Literature 6: Japanese Patent No. 4487068
Non Patent Literature 1: Kaymakcalan et al., Clin. Immunol., Vol. 131, 308-316, 2009

Non Patent Literature 2: Papadopoulos et al., Angiogenesis, Vol. 15, 171-185, 2012

Non Patent Literature 3: Seo et al., Nature Biotechnol., Vol. 23, 731-735, 2005

Non Patent Literature 4: Yuichi Kanehiro et al.: Abstract of Annual Meeting, The Society for Biotechnology, Japan, p. 109, 2008.

Non Patent Literature 5: Sigal et al., Annu. Rev. Immunol. Vol. 10, 519-560, 1992

SUMMARY OF INVENTION

Technical Problem

Taking into consideration the above-described circumstances, it is an object of the present invention to provide a method for obtaining an antibody from an avian B cell antibody library, and more specifically, to provide a method for obtaining an antibody having high affinity from an avian B cell antibody library.

Solution to Problem

The present inventors have conducted intensive studies directed towards obtaining an antibody having high affinity to a target antigen. As a result, the inventors have reacted an avian B cell antibody library with a target antigen in the presence of a calcineurin inhibitor and avian serum, have selected B cells that generate an antigen-specific antibody, and have then cultured the B cells together with a calcineurin inhibitor and avian serum, so that the inventors have succeeded in obtaining an antibody with high affinity.

The calcineurin inhibitor has been used as an immunosuppressive agent in organ transplantation and the treatment of autoimmune disease. It has been known that FK506 and cyclosporin A, which are calcineurin inhibitors, specifically bind to FKBP and cyclophilin, respectively, to form a complex with calcineurin, thereby suppressing activation of T cells. It is said that, in B cells, calcineurin is associated with differentiation or growth of the B cells (Non Patent Literature 5). However, the effects provided by the calcineurin inhibitor have not yet been well known.

Under the aforementioned circumstances, the present inventors have found that an antibody exhibiting high affinity to an antigen can be obtained by obtaining B cells that generate an antibody specifically binding to a target antigen from an avian B cell antibody library in the presence of a calcineurin inhibitor and avian serum, thereby completing the present invention.

Therefore, the present invention includes the following (1) to (8).
(1) A method for obtaining an antibody from an avian B cell antibody library, comprising the following steps (a) to (d):
(a) a step of allowing an avian B cell antibody library to come into contact with an antigen in the presence of a calcineurin inhibitor and avian serum,
(b) a step of selecting avian B cells that bind to the antigen in the step (a),
(c) a step of culturing the avian B cells selected in the step (b) in the presence of a calcineurin inhibitor and avian serum, and
(d) a step of obtaining the avian B cells obtained through the step (c) and/or an antibody expressed by the avian B cells.
(2) The method according to the above (1), further comprising a step of determining the amino acid sequences of the light chain and/or heavy chain variable regions of the antibody expressed by the avian B cells obtained in the step (d).
(3) The method according to the above (1), which is characterized in that the avian B cells are chicken B cells.
(4) The method according to the above (3), which is characterized in that the chicken B cells are DT40 cells.
(5) The method according to any one of the above (1) to (4), which is characterized in that an antibody having a dissociation constant of $1 \times 10^{-8}$ M or less is obtained.
(6) The method according to any one of the above (1) to (5), which is characterized in that the calcineurin inhibitor is FK506 and/or cyclosporin A.
(7) The method according to any one of the above (1) to (6), which is characterized in that the antibody expressed by the avian B cells is IgM or IgG.
(8) The method according to any one of the above (1) to (7), which is characterized in that the antibody expressed by the avian B cells is an avian antibody, a chimeric antibody, a humanized antibody, or a human antibody.

Advantageous Effects of Invention

According to the method of the present invention, it becomes possible to simply and promptly obtain an antibody having high affinity to a target antigen.

BRIEF DESCRIPTION OF DRAWINGS

FIG. 1 shows cytograms obtained by performing single cell sorting in a medium supplemented with avian serum (CS) and FK506 (hereinafter referred to as a "CS/FK506 medium") (a), and in a medium not supplemented with CS and FK506 (hereinafter referred to as a "CS(-) medium") (b).

FIG. 2 shows examples of the results of antigen solid phase ELISA, using the culture supernatants of a CS/FK506 medium reaction group (a) and a CS(-) medium reaction group (b). The horizontal axis indicates clone number. hVEGF-A is used as an antigen, and hTNF-alpha, Lysozyme, and Streptavidin (which is referred to as "SA" in the figure) are used as negative antigens.

Regarding clones in the CS(-) group or the CS/FK506 group, a comparison was made in terms of the mean value of each parameter ((a) kon, (b) koff, and (c) KD).

The response units (RU) of Binding and Stability in the CS(-) group, the CS/FK506 group, and the common group were plotted. The solid line indicates the CS(-) group, and the dotted line indicates the CS/FK506 group, respectively.

DESCRIPTION OF EMBODIMENTS

The embodiment of the present invention relates to a method for obtaining an antibody from an avian B cell antibody library, in particular, a method for obtaining an antibody with high affinity, wherein the method comprises the following steps (a) to (d):

(a) a step of allowing an avian B cell antibody library to come into contact with an antigen in the presence of a calcineurin inhibitor (for example, FK506 or cyclosporin A, etc.) and avian serum,
(b) a step of selecting avian B cells that bind to the antigen in the step (a),
(c) a step of culturing the avian B cells selected in the step (b) in the presence of a calcineurin inhibitor (for example, FK506 or cyclosporin A, etc.) and avian serum, and
(d) a step of obtaining the avian B cells obtained through the step (c) and/or an antibody expressed by the avian B cells.

In the present description, the phrase "in the presence of a calcineurin inhibitor and avian serum" means a state in which a calcineurin inhibitor and avian serum are present in a medium or a solution. Examples of the calcineurin inhibitor include a compound (with a low molecular weight, middle molecular weight, or high molecular weight), a protein, a peptide, and a nucleic acid, which are capable of inhibiting the activity of calcineurin. Moreover, a compound (with a low molecular weight, middle molecular weight, or high molecular weight), a protein, a peptide, a nucleic acid, and the like, which reduce or eliminate the expression of calcineurin, may also be used as calcineurin inhibitors. Preferred examples of the calcineurin inhibitor include cyclosporin A and FK506, and further, an analog of cyclosporin A or an analog of FK506 may also be used. The concentration of the calcineurin inhibitor in a medium or a solution is not particularly limited. For example, cyclosporin A is desirably used in a concentration of 5 nM or less, and FK506 is desirably used in a concentration of 1 µM or less.

Besides, other than the method of adding an inhibitor of calcineurin, avian B cells, in which the expression of calcineurin has been reduced or eliminated, may also be used, and thereby, it is also possible to obtain the effects equivalent to those in the presence of a calcineurin inhibitor.

The used avian serum is preferably chicken serum, and either the serum of an adult bird or the serum of a young bird can be utilized. The concentration of avian serum used is not limited, and it is desirable to use the avian serum in a concentration of, for example, 10% or less, and more preferably, 5% or less. The calcineurin inhibitor and avian serum are desirably added in the steps (a) and (c), but they may be or may not be added in the steps (b) and/or (d).

The "avian B cell antibody library" used the present embodiment is a population of avian B cells generating a variety of antibodies. Besides, in the present description, the "avian B cell antibody library" includes not only a population of avian B cells generating different antibodies, but also a population of avian B cells generating antibodies of a single type. Herein, the avian B cells are not particularly limited, and examples of the avian B cells include DT40 cells as a cell line derived from chicken B cells and biological-origin chicken B cells. Moreover, examples of the avian B cells also include avian B cells, on which a treatment of introducing a variety of mutations has been performed, such as avian B cells, in which an XRCC3 gene has been inactivated (JP Patent Publication (Kokai) No. 2009-060850 A), avian B cells, in which the expression of an AID gene has been controlled (JP Patent Publication (Kokai) No. 2006-109711 A), avian B cells, in which an antibody sequence has been diversified using a HDAC (Histone Deacetylase) inhibitor comprising TSA (Trichostatin A), and avian B cells, in which a foreign gene sequence or a portion thereof has been introduced onto the chromosome thereof (e.g., avian B cells, into which any given antibody gene sequence, etc. has been introduced).

The culture, etc. of the "avian B cell antibody library" used the present embodiment can be easily carried out according to a method well known to a person skilled in the art, and thus, the culture conditions, etc. are not particularly limited. For example, in a case where the avian B cells are DT40 cells, IMDM medium (Invitrogen), etc. may be used, and the cells may be cultured in the presence of about 5% $CO_2$ at approximately 39.5° C.

In addition, the above-described "avian B cell antibody library" may also have been cultured, in advance, in the presence of a calcineurin inhibitor (for example, FK506, etc.) and avian serum, before it is allowed to come into contact with an antigen.

In the present embodiment, examples of the "antibody generated from avian B cells" include an avian antibody, a chimeric antibody, a humanized antibody, and a human antibody. In the present description, the chimeric antibody is an antibody formed by linking regions having different origins to each other, and examples of the chimeric antibody include an antibody formed by linking a variable region to a constant region, the origins of which are different from each other, and an antibody formed by linking a Fab region to a Fc region, the origins of which are different from each other, but are not limited thereto. For instance, a bird-mouse chimeric antibody is an antibody formed by linking the amino acid sequence of an avian gene-derived antibody to the amino acid sequence of a mouse gene-derived antibody. Other examples of the chimeric antibody include: a bird-human chimeric antibody formed by linking the amino acid sequence of an avian gene-derived antibody to the amino acid sequence of a human gene-derived antibody; a bird-rabbit chimeric antibody formed by linking the amino acid sequence of an avian gene-derived antibody to the amino acid sequence of a rabbit gene-derived antibody; and a bird-goat chimeric antibody formed by linking the amino acid sequence of an avian gene-derived antibody to the amino acid sequence of a goat gene-derived antibody.

The humanized antibody is an antibody, in which among the amino acid sequences of the heavy or light chains of a generated antibody, some sequences are avian gene-derived sequences, and other sequences are human gene-derived sequences. On the other hand, the human antibody is an antibody, in which all of the amino acid sequences of the heavy or light chains of a generated antibody are human gene-derived sequences.

Moreover, in the present embodiment, the "antibody generated from avian B cells" includes antibodies comprising the entire or a part of the amino acid sequences of antibodies derived from animal species other than birds. Specific examples include, but are not limited to, antibodies comprising the entire or a part of the amino acid sequences of antibodies obtained from a mouse, a rat, a rabbit, a bovine, a goat, and the like.

In the present embodiment, the isotypes of the "antibody generated from avian B cells" are not particularly limited. Examples of such an isotype include IgM, IgG, IgA, and IgY.

In the present embodiment, the "high-affinity antibody" means an antibody having high binding affinity to an antigen. Dissociation constant (KD) is commonly used as an index of the binding affinity of an antibody. An example of preferred binding affinity is, but is not particularly limited to, affinity having a dissociation constant of $1 \times 10^{-5}$ M or less, $1 \times 10^{-6}$ M or less, $1 \times 10^{-7}$ M or less, $1 \times 10^{-8}$ M or less, $1 \times 10^{-9}$ M or less, $1 \times 10^{-10}$ M or less, or $1 \times 10^{-11}$ M or less. The dissociation constant may also be $1\times10^{-15}$M or more, $1\times10^{-14}$M or more, $1\times10^{-13}$M or more, $1\times10^{-12}$M or more, $1\times10^{-11}$M or more, $1\times10^{-10}$M or more, or $1\times10^{-9}$M or more. Such affinity can be measured by a method well known to a person skilled in the art, and in general, the measurement method is desirably an SPR method, and other than SPR, a BLI method (bio-layer interferometry) can also be applied. Moreover, the affinity can also be measured by an equilibrium method, and examples of such an equilibrium method that may be applied herein include FCM (Flow Cytometry) and ELISA (Enzyme-Linked ImmunoSorbent Assay).

Examples of the "antigen" used in the present embodiment include a compound (with a low molecular weight, middle molecular weight, or high molecular weight), a protein, a peptide, a lipid, and a nucleic acid. The "antigen" used herein may also be, for example, a labeled compound, a complex of a compound and a protein, a complex of a compound and an antibody, a complex of a protein and an antibody, etc. The protein may be a protein secreted into body fluid, a protein expressed on the surface of a cell, a protein presented by bacteria, virus, a virus-like particle or a lipoparticle, or a protein reconstructed from a membrane protein such as Nanodisc. For instance, a cytokine, a growth factor, a hormone, a receptor, or the like can be used. In addition, in the case of obtaining an anti-antibody, an antibody can be used as an antigen. In the case of using an antibody as an antigen, a monoclonal antibody, a chimeric antibody, a humanized antibody, a human antibody, or the like can be used. With regard to the shape of an antibody, a full-length antibody, an antibody fragment (for example, F(ab')2, Fab', Fab, Fv, scFv, Fc, etc.), a protein comprising the amino acid sequences of the variable regions of the heavy chain and/or light chain of an antibody, and the like can be used, but are not limited thereto. The antigen may be subjected to chemical modification such as post-translational modification, and the modification may be carried out, for example, with sugar, phosphoric acid, or lipid.

In the present embodiment, the phrase "to allow an avian B cell antibody library to come into contact with an antigen" means creation of a state, in which a cell (group) constituting the library may be allowed to come into contact (interact) with an antigen, or creation of a state, in which an antibody expressed on the surface of the cell (group) or an antibody secreted from the cell may be allowed to come into contact (interact) with an antigen. For example, the contact of the avian B cell antibody library with the antigen can be carried out by adding an appropriate amount of antigen into a medium or a solution of the library and then culturing the mixture for a suitable period of time, although the contact method is not limited thereto.

As an antigen used herein, a labeled antigen or a tagged antigen can be used. Examples of the labeled antigen that can be used herein include: an antigen that is directly labeled with Biotin or a fluorescent dye; and an antigen that is indirectly labeled through an antibody or the like. Examples of the tagged antigen that can be used herein include antigens, to which a tag such as a FLAG-tag, a His-tag, a Myc-tag, a Strep-tag, GST (glutathione S-transferase), MBP (maltose binding protein) or GFP (green fluorescent protein) has been added.

In the "step of selecting avian B cells that bind to an antigen" of the present embodiment, a method of selecting avian B cells that bind to a labeled antigen or a tagged antigen, using magnetic beads on which specific antibodies, proteins or compounds are immobilized, can be preferably applied. For example, antigen-bound avian B cells may be selected using Dynabeads (registered trademark) (Thermo Fisher) or MACS microbeads (Miltenyi Biotec), or may also be selected using a fluorescently-labeled anti-tag antibody or the like.

In the "step of culturing the selected avian B cells in the presence of a calcineurin inhibitor and avian serum" of the present embodiment, the time of culturing the avian B cells in the presence of a calcineurin inhibitor and avian serum is not particularly limited, and it may be, for example, approximately 1 to 168 hours.

In the present embodiment, the avian B cells obtained as a result of culturing the selected avian B cells in the presence of a calcineurin inhibitor (for example, FK506 or cyclosporin A, etc.) and avian serum include avian B cells expressing a high-affinity antibody. The antibody secreted from the avian B cells can be obtained as a high-affinity antibody, and then, by determining the gene sequences of the heavy chain and light chain of the antibody expressed by the avian B cells, the gene sequence of the high-affinity antibody can be obtained.

Besides, the avian B cells are cultured in a medium that is not supplemented with a calcineurin inhibitor and avian serum to obtain a "control group," whereas the avian B cells are cultured in a medium supplemented with a calcineurin inhibitor and avian serum to obtain a "calcineurin inhibitor/avian serum group." Thereafter, the amino acid sequences of the light chain variable region and/or heavy chain variable region of antibodies expressed by the two above groups are determined. Thereafter, the antibody expressed by avian B cells derived from the "calcineurin inhibitor/avian serum group" that expresses an antibody having an amino acid sequence different from that of the "control group" may be selected as a candidate of high-affinity antibody.

The disclosures of all publications cited in the present description are incorporated herein by reference in their entirety. In addition, throughout the present description, when singular terms such as "a," "an," and "the" are used, these terms include not only single items but also multiple items, unless otherwise clearly specified.

Hereinafter, the present invention will be further described in the following examples. However, these examples are only illustrative examples of the embodiments of the present invention, and thus, are not intended to limit the scope of the present invention.

EXAMPLES

Selection of High-Affinity Antibody
1. Construction of Antigen Expression Vector The gene sequence of VEGF 165 as one isoform of human VEGF-A (27-191 amino acid sequence, UniProt# P15692-4, hereinafter referred to as "hVEGF-A") and the gene sequence of human TNF-alpha (77-233 amino acid sequence, UniProt# P01375, hereinafter referred to as "hTNF-alpha") were synthesized. According to PCR, a FLAG tag was added to the N-terminus of each sequence, and then, they were each inserted into a pEF1 vector (V92020, Invitrogen) to obtain expression vectors, FLAG-hVEGF-A/pEF1 and FLAG-hTNF-alpha/pEF1.

2. Gene Introduction and Expression

The gene introduction method was carried out in accordance with the protocols of NeoFection (N462, ASTEC CO., LTD.). FreeStyle 293F cells (R790-07, Life Technologies) ($1.0\times10^6$ cells/mL), which had been transfected with the expression vectors (FLAG-hVEGF-A/pEF1 and FLAG-hTNF-alpha/pEF1) using NeoFection, were subjected to shaking culture at 37° C., in the presence of 8% $CO_2$ for 5 days, in 3 L of a culture solution (BioShaker CO2-BR-180LF, TAITEC). For the culture, FreeStyle 293 Expression Medium (12338-026, Life technologies) and 1% Penicillin-Streptomycin (15140-122, Life technologies) were used.

3. Purification of Antigen

Each culture supernatant (3 L) was recovered, was then adsorbed on ANTI-FLAG M2 Affinity Gel (A2220-25ML, SIGMA), and was then washed with D-PBS(−) (045-29795, Wako). Thereafter, the resultant was eluted with 0.1 mg/mL FLAG peptide (F-3290, SIGMA) and D-PBS(−). Each fraction and flow-through fraction were confirmed by SDS-PAGE and Western Blotting using Monoclonal ANTI-FLAG M2 antibody produced in mouse (F3165-1MG, SIGMA). A fraction comprising a protein of interest was recovered, was then concentrated using Amicon Ultra-15 10K (UFC901024, Millipore), and was then filtrated through a 0.22-μm filter (MILLEX-GV, SLGVJ13SL, Millipore).

The concentrated FLAG purification sample was eluted from D-PBS(−), using a 120-mL gel filtration column, HiLoad 16/600 Superdex 200 pg (28-9893-35, GE Healthcare). Each fraction was observed by SDS-PAGE, and as a result, it was confirmed that the protein of interest was purified.

After completion of gel filtration and purification, the sample was concentrated using Amicon Ultra-15 10K, and was then filtrated through a 0.22-μm filter. The concentration of the protein in each of the purified antigens (hVEGF-A and hTNF-alpha) was calculated using NanoDrop Spectrophotometer ND-2000c.

4. Culture of Library

The method of culturing a human library using, as a host, a DT40 cell that is a chicken B cell-derived cell line was carried out by the following method. The cells were cultured at 39.5° C., in the presence of 5% $CO_2$. As a medium, IMDM (12440-079, Life Technologies), which was supplemented with 10% FBS (11824, Biosera) and 1% Penicillin-Streptomycin, was used. Hereafter, a CS(−) medium indicates the aforementioned medium, unless otherwise specified. On the other hand, a CS/FK506-supplemented medium indicates a CS(−) medium, to which 5% avian serum (16110-082, Life Technologies) and 1 μM FK506 (1007965, Cayman) are added.

Figure 1:
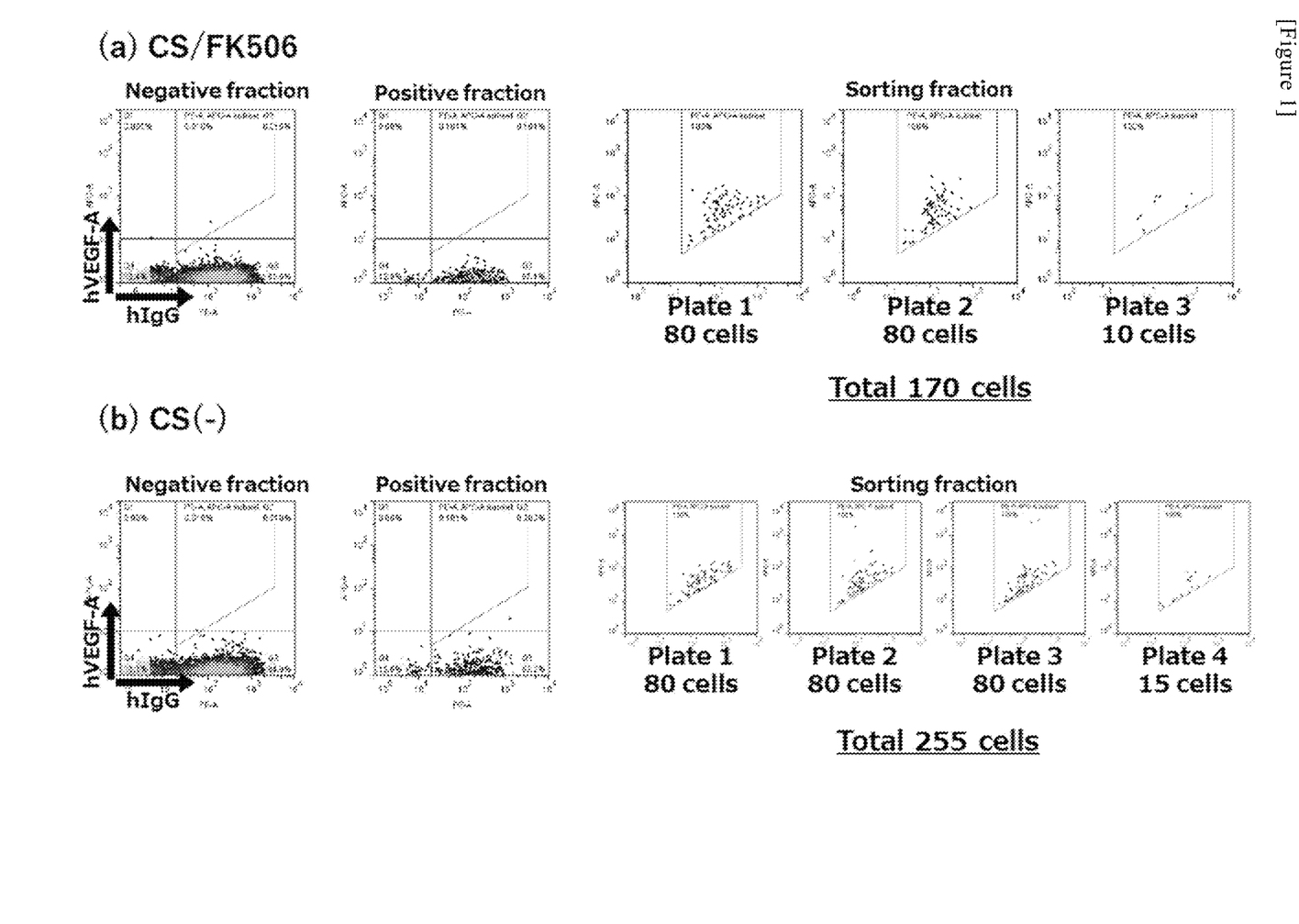
FIG. 1 shows the results of single cell sorting.

5. Specific Adsorption Using Magnetic Beads and Continuous Cell Sorting Using Flow Cytometer As a library, the human library described in WO2015/167011 was used. Two sets of libraries were prepared, and one of the libraries was suspended in the CS/FK506-supplemented medium, and the other library was suspended in the CS(−) medium. To the library suspended in each medium, the hVEGF-A antigen (final concentration: 10 nM) and a biotin-labeled anti-FLAG antibody (F9291-1MG, SIGMA) (amount: 1/500) were added, and the thus obtained mixture was then reacted at 4° C. for 30 minutes, while performing inversion mixing. After completion of the reaction, the resultant was washed twice with each medium, and was then suspended again in each medium. Anti-Biotin MicroBeads UltraPure (130-105-637, Miltenyi Biotec) (amount: 1/100), Goat Anti-Human IgG-PE (2040-09, SouthernBiotech) (amount: 1/10000), and Streptavidin Alexa Fluor 647 Conjugate (S21374, Life Technologies) (amount: 1/1000) were added to the suspension, and the obtained mixture was then reacted at 4° C. for 10 to 30 minutes, while performing inversion mixing. After completion of the reaction, column concentration was carried out using autoMACS Pro Separator (Miltenyi Biotec), and a fraction that was not adsorbed on the column (negative fraction) was measured using FACS Aria Fusion (BD), so that the sorting range was set. Thereafter, a total amount of positive fraction sample was loaded, and sorting was then carried out, so that a positive cell population could be added, in an amount of a single cell/well, into a 96-well plate, into which each medium had been dispensed (FIG. 1). Regarding the CS/FK506-supplemented medium reaction group, 170 wells (a single cell/well) were sorted to the CS/FK506-supplemented medium. Regarding the CS(−) medium reaction group, 255 wells (a single cell/well) were sorted to the CS(−) medium.

6. Screening According to Antigen Solid Phase ELISA

A hVEGF-A antigen solution and a negative control antigen solution (20 μL each), which had been diluted to 2.5 μg/mL with D-PBS(−) (14249-24, Nacalai Tesque, Inc.), were each dispensed in MAXISORP 384 IMMUNO PLATE (464718, NUNC), and were then reacted at 4° C., overnight, for consolidation. Thereafter, the solution was removed by centrifugation using a small centrifuge specialized for microplates (GYRO mini GM-01, MICRONIX), and 45 μL of a blocking solution (PBS containing 1% BSA (A8022, SIGMA)) was then added to the residue, followed by performing a reaction at room temperature for 1 hour. After that, the solution was removed by centrifugation with GYRO mini, and 25 μL of a culture supernatant was then added to the residue, followed by performing a reaction at room temperature for 1 hour. After that, the solution was removed by centrifugation with GYRO mini, and 25 μL of Goat anti-Human IgG-Fc HRP-conjugated (A80-104P, BETHYL), which had been 2000 times diluted with a blocking solution, was then added to the residue, followed by performing a reaction at room temperature for 45 minutes. Subsequently, the resultant was washed with a washing solution (PBS containing 0.05% Tween20 (167-11515, Wako)) five times, and 25 μL of TMB (53-00-02, KPL) was then added to the resultant, followed by performing a reaction for 5.5 minutes. Thereafter, 25 μL of 1 N sulfuric acid (192-04696, Wako) was added to the reaction solution to terminate the reaction, and the absorbance at 450 nm was then measured using a microplate reader (infinite M1000, TECAN). As negative antigens, the prepared hTNF-alpha, Lysozyme (L6876, SIGMA), and Streptavidin (32243-24, Nacalai Tesque, Inc., indicated as "SA" in the figure) were used. A correction value obtained by subtracting the background from the obtained absorbance was used as OD, and the S/N ratio indicates a value obtained according to the formula: OD (hVEGF-A)/OD (hTNF-alpha).

Figure 2:
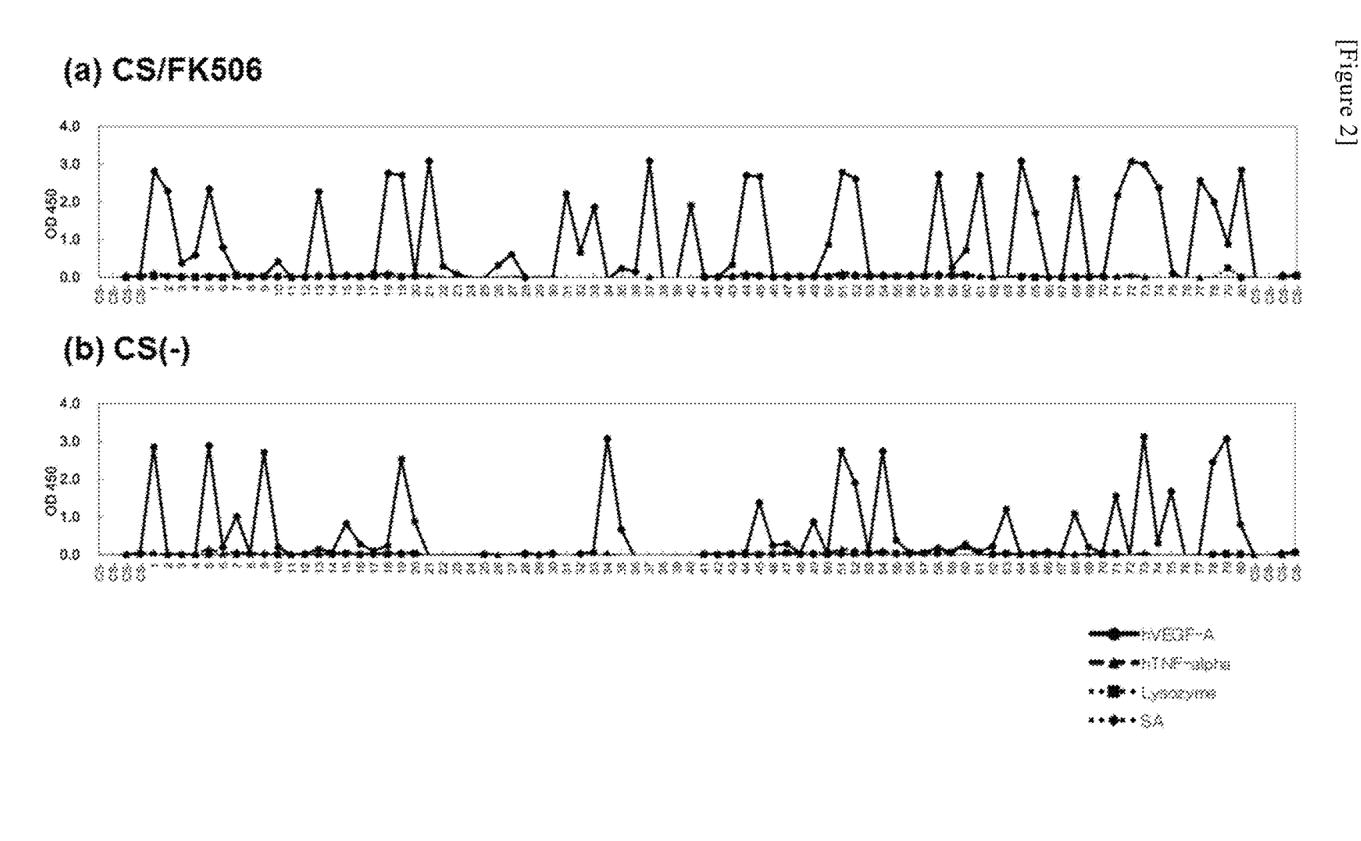
FIG. 2 shows antigen solid phase ELISA screening.

The CS/FK506-supplemented medium reaction group was cultured for 6 days after completion of the sorting, and was then subjected to antigen solid phase ELISA. Colony formation was confirmed in 113 wells out of the sorted 170 wells, and in the 113 wells, 63 clones specifically reacting with antigens (OD>1; S/N ratio >10) were confirmed (Table 1 and FIG. 2).

The CS(−) medium reaction group was cultured for 7 days after completion of the sorting, and was then subjected to antigen solid phase ELISA. Colony formation was confirmed in 148 wells out of the sorted 255 wells, and in the 148 wells, 43 clones specifically reacting with antigens (OD>1; S/N ratio >10) were confirmed (Table 1 and FIG. 2).

TABLE 1

| Conditions | Number of sorted well | Number of growing colonies | Growth rate | Positive number | |
|---|---|---|---|---|---|
| | | | | OD > 1 | OD > 0.2 |
| CS/FK506 | 170 | 113 | 66.5% | 63 | 78 |
| CS (—) | 255 | 148 | 58.0% | 43 | 75 |

7. Sequence Analysis and Grouping

All of the positive clones, which satisfied the standards (OD>1, and S/N ratio >10), were analyzed in terms of the antibody sequence of the variable region thereof, and the positive clones whose variable regions including those of the heavy and light chains encoded the same amino acid sequence were classified in one group. According to this method, grouping was carried out. Finally, it was confirmed that there were 16 types of CS/FK506-supplemented medium reaction groups and 16 types of CS(−) medium reaction groups. Among them, 6 types were confirmed to be present in the two above groups (Table 2). Hereinafter, the group having a common sequence in both groups was referred to as a "common group," and sequence groups, in which such a common group was removed from the CS(−) medium reaction group and the CS/FK506-supplemented medium reaction group, were referred to as a "CS(−) group" and a "CS/FK506 group," respectively.

TABLE 2

| Sequence group | Number of groups |
| --- | --- |
| CS/FK506 group | 10 |
| CS(—) group | 10 |
| Common group | 6 |

8. Affinity Screening

Figure 3:
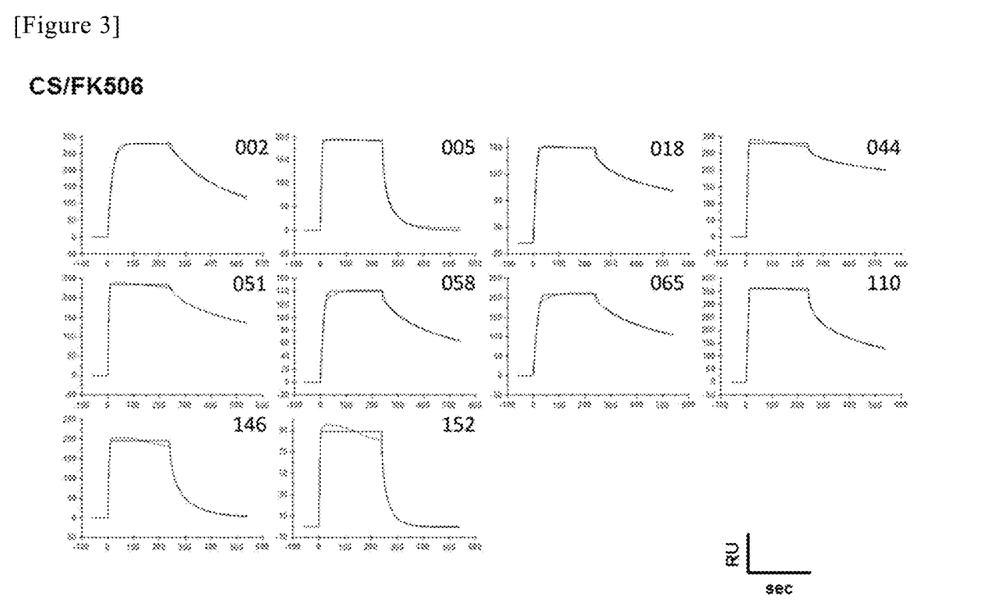
FIG. 3 shows the results of the SPR sensorgrams of a CS/FK506 group (10 types). Clone number is shown in the upper right portion of each sensorgram.
Figure 4:
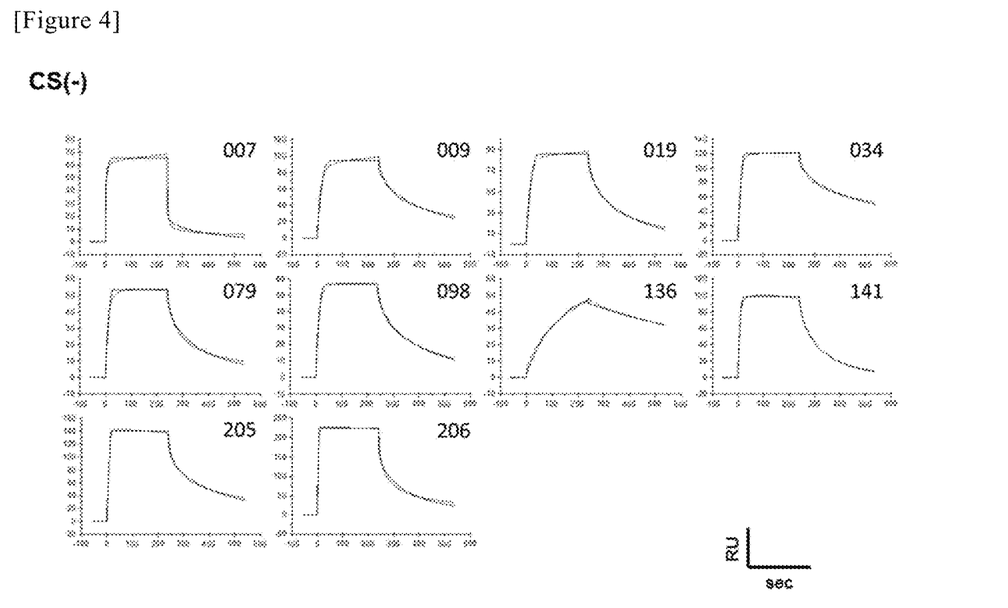
FIG. 4 shows the results of the SPR sensorgrams of a CS(-) group (10 types).
Figure 5:
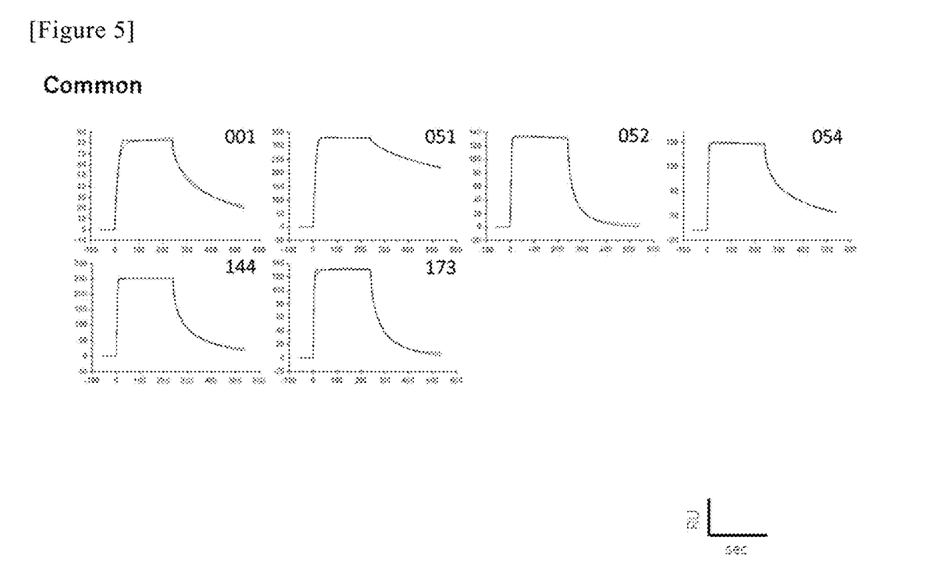
FIG. 5 shows the results of the SPR sensorgrams of a common group (6 types).

With regard to the representative 26 types of clones of the individual sequence groups, a culture supernatant was prepared again, and the affinity to the antigen was then measured according to a SPR method (Biacore T200, GE Healthcare). Using Human Antibody Capture Kit (BR100839, GE Healthcare), an anti-human IgG (Fc) antibody was immobilized on a CM5 sensor chip (BR100530, GE Healthcare), and the antibody in the culture supernatant was then captured. Thereafter, 100 nM hVEGF-A was allowed to react therewith for 240 seconds and was then dissociated for 300 seconds. After that, as a regeneration solution, 3M MgCl$_2$ was allowed to react with the resultant for 30 seconds, and thus, one cycle was completed. As a buffer, HBS-EP+(10 mM HEPES, 150 mM NaCl, 3 mM EDTA, and 0.05% (v/v) surfactant P20 (pH 7.4) (BR100669, GE Healthcare)) was used, and the measurement was carried out at a flow rate of 30 μL/min. Several clones were measured again using 30 nM hVEGF-A according to the same protocols as those described above. The SPR sensorgrams of antibodies obtained from the representative clones of individual sequence groups were compared with one another. As a result, many clones showed a box-shape sensorgram having a large association rate and a large dissociation rate, but several clones showed an extremely low dissociation rate (FIG. 3 to FIG. 5).

Figure 6:
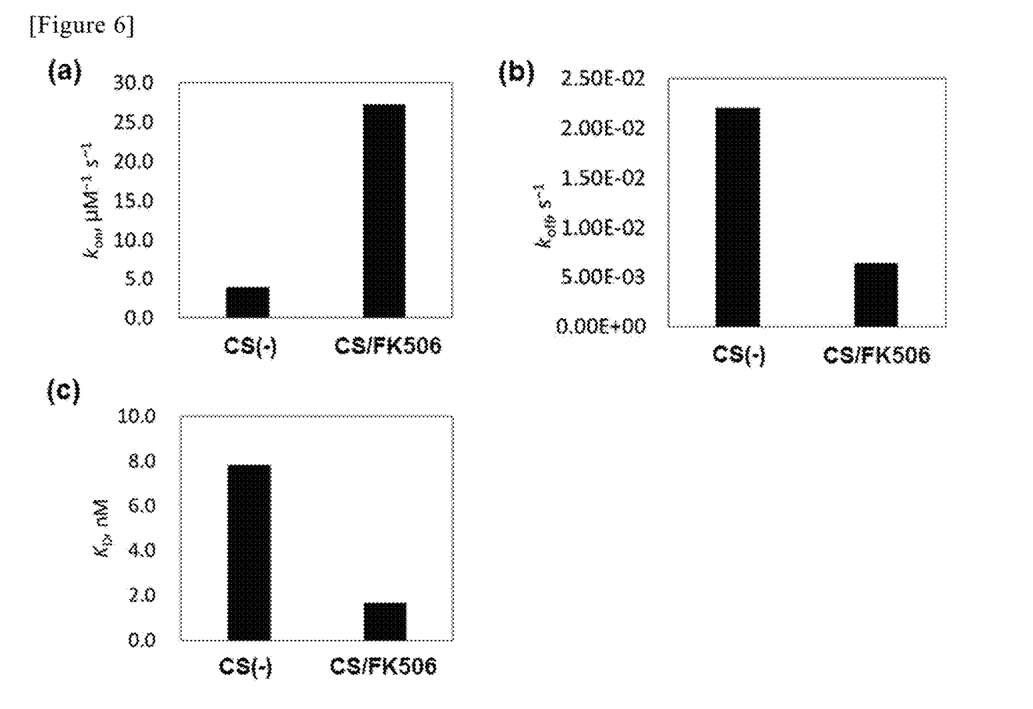
FIG. 6 shows an association rate constant (kon), a dissociation rate constant (koff), and a KD value, which are obtained between an antigen and an antibody.

Employing Biacore T200 Evaluation Software, fitting was carried out on each SPR sensorgram according to a Langmuir 1:1 binding model, so as to calculate the association rate constant kon and the dissociation rate constant koff. Then, according to the equation: KD=koff/kon, the KD value was determined. The clones of the CS(−) group and the CS/FK506 group were compared with one another, in terms of the mean value of each parameter (FIG. 6). As a result, the kon value was larger and the koff value was smaller in the CS/FK506 group than in the CS(−) group, and the KD value was approximately 4.7 times smaller in the CS/FK506 group than in the CS(−) group (Table 3).

TABLE 3

| Group | kon (1/Ms) | koff (1/s) | KD (M) |
| --- | --- | --- | --- |
| CS/FK506 group | 2.73E+07 | 6.39E−03 | 1.66E−09 |
| CS(—) group | 3.87E+06 | 2.20E−02 | 7.83E−09 |

Figure 7:
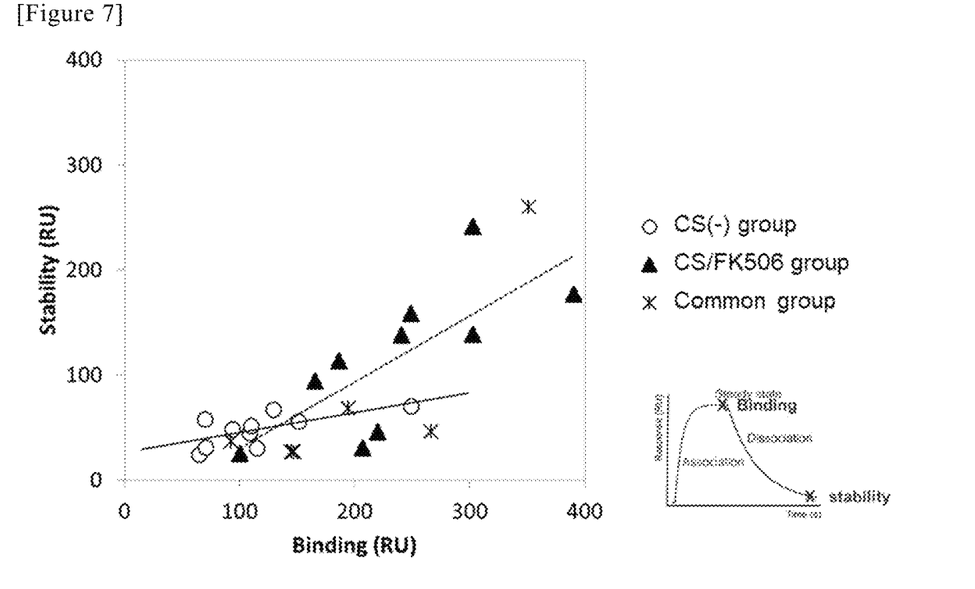
FIG. 7 shows a correlation plot of stability with respect to the binding between an antigen and an antibody.

Furthermore, in order to confirm the dissociation rate of the antibody, the response unit (RU) 5 seconds before termination of the measurement of the association reaction in the obtained sensorgram was defined as "Binding," and the RU 5 seconds before termination of the dissociation reaction was defined as "Stability," and the correlation of Stability to Binding was plotted (FIG. 7). As a result, it was revealed that the Stability value was higher in the CS/FK506 group than in the CS(−) group, namely, that there were many clones having a slow dissociation rate. In addition, the inclination was calculated from the approximation formula of each group according to linear regression, and individual groups were then compared in terms of the dissociation percentage of an antibody-antigen complex. As a result, the dissociation percentage was lower in the CS/FK506 group than in the CS(−) group (Table 4). These results suggest that, in the CS/FK506 group, the antibody should bind to the antigen even after initiation of the dissociation reaction with high probability.

TABLE 4

| Group | Inclination | Dissociation percentage (%) |
| --- | --- | --- |
| CS(—) group | 0.19 | 81 |
| CS/FK506 group | 0.63 | 37 |

INDUSTRIAL APPLICABILITY

The present invention relates to a method for obtaining an antibody that binds to an antigen of interest with high affinity. Therefore, it is expected that the present invention will be utilized in the field of medicine and pharmacy that are associated with antibody drugs, or in the field of using antibodies as research reagents.

The invention claimed is:

1. A method for obtaining an antibody from an avian B cell antibody library, comprising:
   (a) allowing an avian B cell antibody library to come into contact with an antigen in the presence of a calcineurin inhibitor and avian serum,
   (b) selecting avian B cells that bind to the antigen in (a),
   (c) culturing the avian B cells selected in (b) in the presence of a calcineurin inhibitor and avian serum, and
   (d) obtaining the avian B cells obtained through (c) and/or an antibody expressed by the avian B cells.

2. The method according to claim 1, further comprising determining the amino acid sequences of the light chain and/or heavy chain variable regions of the antibody expressed by the avian B cells obtained in (d).

3. The method according to claim 1, wherein the avian B cells are chicken B cells.

4. The method according to claim 3, wherein the chicken B cells are DT40 cells.

5. The method according to claim 1, wherein an antibody having a dissociation constant of $1 \times 10^{-8}$ M or less is obtained.

6. The method according to claim 1, wherein the calcineurin inhibitor is FK506 and/or cyclosporin A.

7. The method according to claim 1, wherein the antibody expressed by the avian B cells is IgM or IgG.

8. The method according to claim 1, wherein the antibody expressed by the avian B cells is an avian antibody, a chimeric antibody, a humanized antibody, or a human antibody.

* * * * *